United States Patent [19]

Okamura et al.

[11] Patent Number: 4,673,632

[45] Date of Patent: Jun. 16, 1987

[54] HARDENING METHOD FOR GELATIN

[75] Inventors: Hisashi Okamura; Hiroshi Kawamoto; Hisashi Shiraishi, all of Kanagawa, Japan

[73] Assignee: Fuji Photo Film Co., Ltd., Kanagawa, Japan

[21] Appl. No.: 726,441

[22] Filed: Apr. 23, 1985

[30] Foreign Application Priority Data

Apr. 23, 1984 [JP] Japan ................... 59-82215

[51] Int. Cl.⁴ .......................... C08F 3/34; C08H 1/06; C09H 7/00; G03C 1/30
[52] U.S. Cl. .................................. 430/510; 430/621; 430/623; 530/354
[58] Field of Search ............... 430/621, 623, 626, 510; 260/117, 112 R, 91.3 VA; 530/354

[56] References Cited

U.S. PATENT DOCUMENTS 3,826,788 7/1974 Froehlich et al. .................. 260/117
3,992,366 11/1976 Stauner et al. ..................... 260/117
4,111,926 9/1978 Sera et al. .......................... 260/117
4,233,398 11/1980 Nittel et al. ........................ 430/623

FOREIGN PATENT DOCUMENTS 1193290 5/1970 United Kingdom ............... 430/623

Primary Examiner—Won H. Louie
Attorney, Agent, or Firm—Sughrue, Mion, Zinn, Macpeak and Seas

[57] ABSTRACT

A hardening method for gelatin which comprises using as a hardening agent a compound represented by formula (I)

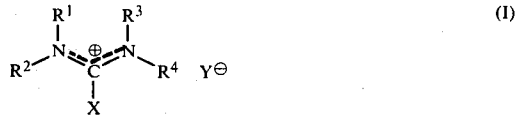

wherein $R^1$, $R^2$, $R^3$, and $R^4$ each represents a substituted or unsubstituted alkyl group, a substituted or unsubstituted alkenyl group, a substituted or unsubstituted aralkyl group, or a substituted or unsubstituted aryl group; or two of said $R^1$, $R^2$, $R^3$, and $R^4$ are combined with each other to form a ring (1); or 3 or more of said $R^1$, $R^2$, $R^3$ and $R^4$ are combined with each other to form a condensed ring (2); X represents a group capable of being released when the compound shown by formula (I) reacts with a nucleophilic reagent; $Y^\ominus$ represents an anion; or $Y^\ominus$ is combined with one of X, $R^1$, $R^2$, $R^3$, and $R^4$, ring (1), or ring (2) to form an anionic portion of an intramolecular salt.

16 Claims, No Drawings

HARDENING METHOD FOR GELATIN

FIELD OF THE INVENTION

This invention relates to a hardening method for gelatin by an improved hardening agent, and more particularly to a hardening method for gelatin which is useful for silver halide photographic materials.

BACKGROUND OF THE INVENTION

Gelatin is used as a binder for various photographic materials. For example, silver halide photographic emulsion layers, protective layers for emulsion layers, filter layers, interlayers, antihalation layers, backing layers, film base subbing layers, baryta layers, etc., of photographic materials use gelatin as the main constitutional component.

Photographic materials containing gelatin are processed using various aqueous solutions having various pH and temperature values. If the layers of photographic materials contain gelatin which is not treated with a hardening agent, the properties of these layers depend mainly upon the properties of gelatin, and are poor in water resistance, excessively swell in an aqueous solution to greatly reduce the mechanical strength. In an extreme case, the gelatin layer is dissolved off in an aqueous solution, e.g., in a high temperature solution (higher than 30° C.) or in a high-alkaline aqueous solution. Such properties are fatal defects as properties of layers constituting photographic materials.

For increasing the water resistance, heat resistance and mechanical strength of a gelatin layer by hardening gelatin, it has hitherto been known that many compounds are effective.

These compounds are known as "hardening agents", and are usually used for the production of photographic materials. They include, for example, aldehyde series compounds such as formaldehyde, glutaraldehyde, etc., compounds having a reactive halogen described, e.g., in U.S. Pat. No. 3,288,775, compounds having a reactive ethylenically unsaturated bond described in, e.g., U.S. Pat. No. 3,642,486, Japanese Patent Publication No. 13,563/'74, aziridine series compounds described, e.g., in U.S. Pat. No. 3,017,280, etc., epoxy compounds described in U.S. Pat. No. 3,091,537, halogencarboxylaldehydes such as mucochloric acid, etc., dioxanes such as dihydroxydioxane, dichlorodioxane, etc., and inorganic hardening agents such as chromium alum, zirconium sulfate, etc.

However, when these known gelatin hardening agents are used for photographic materials, they have defects in that the hardening action is insufficient, the degree of hardening changes for a long period of time due to "post-hardening" (caused by slow continued hardening of the gelatin, bad actions (such as, in particular, the increase of fog, the reduction of sensitivity, etc.) are given to the properties of photographic materials, effects of the hardening agents are reduced by other photographic additives which coexist with the hardening agents, or they reduce the effects of other photographic additives (e.g., couplers for color photographic materials), etc.

Hardening agents showing a relatively high hardening reaction rate and less post hardening include compounds having a dihydroquinoline skeleton as described in Japanese Patent Application (OPI) No. 38,540/'75, corresponding to U.S. Pat. No. 4,013,468 (the term "OPI" used herein indicates an unexamined published patent application open to public inspection); compounds having a phosphorus-halogen bond as described in Japanese Patent Application (OPI) No. 113,929/'83; compounds having an N-sulfonyloxyimido group as described in Japanese Patent Application (OPI) No. 93,470/'77, corresponding to U.S. Pat. No. 4,111,926; and compounds having two or more N-acyloxyimino group in one molecule as described in Japanese Patent Publication No. 22,089/'78, corresponding to U.S. Pat. No. 4,052,373. These hardening agents have excellent properties such that the hardening action proceeds quickly and the occurrence of the so-called post hardening is greatly lessened, but they are poor in water-solubility, whereby they are liable to cause non-uniform hardening in silver halide photographic emulsion layers. Furthermore, since these hardening agents require specific organic solvents in the case of adding the hardening agents to silver halide photographic emulsions or silver halide photographic emulsion layers, the trouble of uneven coating is liable to cause based on the organic solvent as well as the use of an organic solvent requires care for the prevention of explosion.

Hardening agents showing a high hardening reaction for gelatin and having an excellent water solubility include N-carbamoylpyridinium salts as described in Japanese Patent Application (OPI) Nos. 51,945/'74 and 59,625/'76 corresponding respectively to U.K. Pat. No. 1,383,630 and to U.S. Pat. No. 4,063,952; and 2-sulfonyloxypyridinium salts as described in Japanese Patent Application (OPI) No. 110,762/'81.

These hardening agents having features such that a water solubility is high, the hardening action for gelatin is fast, and the occurrence of post-hardening is less. However, these hardening agents show a high hardening reaction rate for gelatin and a side reaction occurs quickly by the decomposition with water. These hardening agents have the fault that the effective use efficiency of the hardening agent is very low in a general production method of photographic materials using an aqueous solution of gelatin; therefore, a large amount of the hardening agent must be used for obtaining gelatin layers having a desired degree of hardening.

It is generally considered that when the hardening agents such as described in Japanese Patent Application (OPI) Nos. 51,945/'74; 59,625/'76 and 110,762/'81 are nucleophilically attacked by a carboxy group or an amino group of gelatin, the hardening agents react with the group to harden the gelatin. In the case of producing gelatin layers, an aqueous solution of gelatin is generally used. In this case, since water has a nucleophilic property to some extent, water reacts with the foregoing hardening agent to decompose the hardening agent, whereby the effect of the hardening agent is inevitably lost. This tendency is particularly severe for a hardening agent showing a fast hardening action.

Accordingly, in order to efficiently and quickly harden gelatin, the development of a hardening agent showing a higher reactivity with a carboxy group or an amino group of gelatin than the reactivity with water in gelatin, that is, having a good selectivity in the reaction with gelatin, is important. Hardening agents such as N-carbamoylpyridinium salts and 2-sulfonyloxypyridinium salts have a fault in that the effective use efficiency of the hardening agent is very low owing to the low selectivity in the reaction with gelatin. Therefore, the development of a hardening agent showing a high effective use efficiency, showing a fast harden reaction rate with gelatin, and having a high water solubility has been ardently desired.

SUMMARY OF THE INVENTION

A first object of this invention is, therefore, to provide a hardening method for gelatin by a novel gelatin hardening agent.

A second object of this invention is to provide a hardening method for gelatin using a hardening agent showing a fast hardening action for gelatin and less post hardening.

A third object of this invention is to provide a hardening method using a hardening agent which has a high solubility in water and can be added to an aqueous hydrophilic colloid solution such as a silver halide photographic emulsion without need of a specific organic solvent.

A fourth object of this invention is to provide a hardening method using a gelatin hardening agent capable of reacting with a reactive residue of gelatin with a high selectivity to effectively harden the gelatin.

As the result of various investigations, the inventors have discovered that the above objects of this invention can be attained by hardening a gelatin using, as a hardening agent, a compound represented by formula (I)

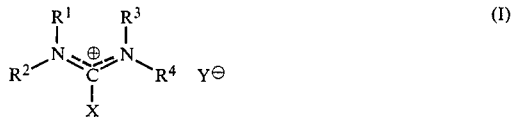

(I)

wherein $R^1$, $R^2$, $R^3$, and $R^4$, which may be the same or different, each represents an alkyl group, an alkenyl group, an aralkyl group, or an aryl group (these groups may be substituted); optional two of $R^1$, $R^2$, $R^3$ and $R^4$ may combine with each other to form a ring or three or more of $R^1$, $R^2$, $R^3$ and $R^4$ may combine with each other to form a condensed ring; X represents a group capable of releasing when the compound shown by general formula (I) reacts with a nucleophilic reagent; and $Y^\ominus$ represents an anion; said $Y^\ominus$ may combine with any one of X, $R^1$, $R^2$, $R^3$, and $R^4$ (or when at least two of $R^1$, $R^2$, $R^3$ and $R^4$ combine with each other to form a ring, $Y^\ominus$ may bond with the ring) to form a intramolecular salt.

DESCRIPTION OF THE PREFERRED EMBODIMENT

The invention will further be explained below in more detail.

In general formula (I), $R^1$, $R^2$, $R^3$ and $R^4$, which may be the same or different, each preferably represents a straight chain or branched alkyl group having 1 to 20 carbon atoms (e.g., a methyl group, an ethyl group, a 2-ethylhexyl group, a dodecyl group, etc.), an aralkyl (including heterocyclic aromatic type) group having from 6 to 20 carbon atoms (e.g, a benzyl group, a phenthyl group, a 3-pyridylmethyl group, etc.), or an aryl (including heterocyclic aromatic type) group having from 5 to 20 carbon atoms (e.g., a phenyl group, a naphthyl group, a pyridyl group, etc.).

Also, $R^1$, $R^2$, $R^3$, and $R^4$ can each have a substituent such as, for example, a halogen atom (e.g., chlorine atom), an alkoxy group, preferably having from 1 to 20 carbon atoms, an aryloxy group, preferably having from 6 to 20 carbon atoms, or an N-N-di-substituted carbamoyl group. Nitrogen atoms of the carbamoyl group are substituted with alkyl groups, aralkyl groups, or aryl groups.

It is preferred that at least one combination of two of $R^1$, $R^2$, $R^3$, and $R^4$ combine with each other to form a ring or rings. Examples of the ring formed by the combination of $R^1$ and $R^2$ and/or $R^3$ and $R^4$ together with nitrogen atom include a 5 to 8 membered nitrogen-containing heterocyclic ring such as a pyrrolidine ring, a piperadine ring, a perhydroazepine ring, a morpholine ring, a pyrrole ring, etc. It is especially preferable that $R^1$ and $R^2$, and $R^3$ and $R^4$ combine with each other to form pyrrolidine rings. Also, examples of the ring formed by the combination of $R^1$ and $R^3$ or $R^2$ and $R^4$ together with two nitrogen atoms and a carbon atoms between the nitrogen atoms include a 5 to 8 membered nitrogen-containing heterocyclic ring such as an imidazoline ring, a tetrahydropyrimidine ring, a tetrahydrodiazepine ring, etc.

Examples of a compound having a condensed ring formed by the combination of two of $R^1$, $R^2$, $R^3$ and $R^4$ include the compounds represented by the formula

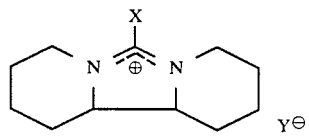

wherein X and $Y^\ominus$ are the same as defined in formula (I).

The above-described heterocyclic rings may be substituted, for example, with a halogen atom, an alkyl group, preferably having from 1 to 20 carbon atoms; an aralkyl group, preferably having from 7 to 20 carbon atoms; an aryl group, preferably having from 6 to 20 carbon atoms; an alkoxy group, preferably having from 1 to 20 carbon atoms; an aralkyloxy group, preferably having from 7 to 20 carbon atoms; and an aryloxy group, preferably having from 6 to 20 carbon atoms.

X In the above formula is a group capable of being released when the compound represented by formula (I) reacts with a nucleophilic reagent and is preferably a halogen atom, a substituted or unsubstituted alkylsulfonyloxy group, preferably having from 1 to 15 carbon atoms (examples of substituents include a halogen atom, an alkoxy group and a heterocyclic aromatic group), a substituted or unsubstituted aralkylsulfonyloxy group, preferably having from 7 to 15 carbon atoms (examples of substituents include a halogen atom and an alkoxy group), a substituted or unsubstituted arylsulfonyloxy group (including heterocyclic aromatic type), preferably having from 6 to 15 carbon atoms (examples for substituent include a halogen atom, an alkyl group and an alkoxy group), a substituted or unsubstituted 1-pyridinio group (examples of substituents include an alkyl group preferably having from 1 to 10 carbon atoms, $-SO_3H$ and $-SO_3^\ominus$). X is especially preferably a chlorine atom, etc.

$Y^\ominus$ in the formula represents an anion and examples of the anion are a halide ion, a sulfonate ion such as substituted or unsubstituted alkylsulfonate ion having from 1 to 15 carbon atoms (examples of substituents include a halogen atom, an alkoxy group and heterocyclic aromatic group), a substituted or unsubstituted aralkylsulfonate ion having from 7 to 15 carbon atoms (examples of substituents include halogen atoms and alkoxy groups) and substituted or unsubstituted arylsulfonate ion (including heterocyclic aromatic type; examples of substituents include a halogen atom, an alkoxy group and an alkyl group), a sulfate ion, a phosphonate ion, a phosphate ion, $BF_4^\ominus$, $ClO_4^\ominus$, $PF_6^\ominus$, etc. In particular, $Cl^\ominus$, $BF_4^\ominus$, $ClO_4^\ominus$, $PF_6^\ominus$, and a sulfonate ion are preferred.

Also, the compound shown by formula (I) above is frequently described as the equilibrium of the two resonance extreme structural formulae of formulae (II) and (III), but due to the steric structure of the molecules, and the electrical effect substituents, etc., the equilibrium may have a structure biased to formula (II) or formula (III).

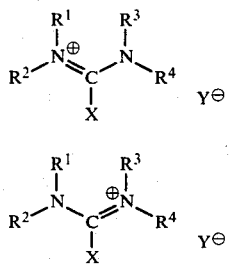

wherein $R^1$, $R^2$, $R^3$, $R^4$, X, and $Y^\ominus$ have the same significance as defined in formula (I).

As an example of the compounds represented by formula (I), such are described in T. Fujisawa et al, *Chemistry Letters*, p.1891(1982) as esterifying agents.

Examples of the aforesaid compound for use in this invention are illustrated below, but the compounds for use in this invention are not limited thereto.

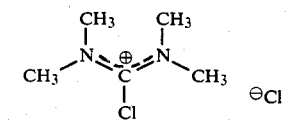 Compound 1

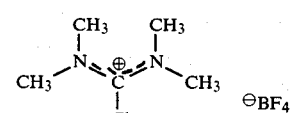 Compound 2

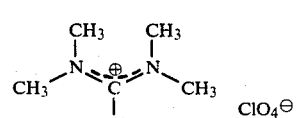 Compound 3

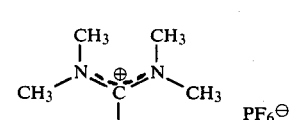 Compound 4

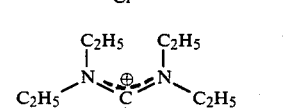 Compound 5

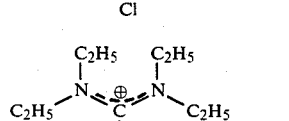 Compound 6

-continued

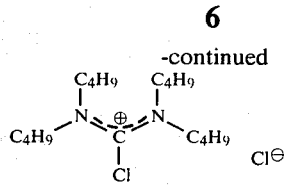 Compound 7

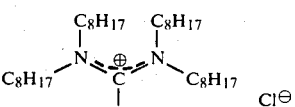 Compound 8

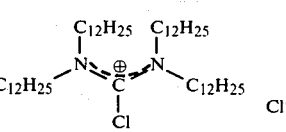 Compound 9

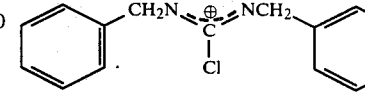 Compound 10

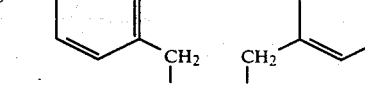 Compound 11

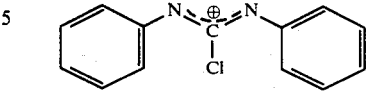 Compound 12

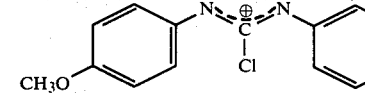 Compound 13

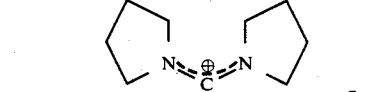 Compound 14

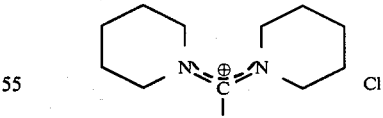 Compound 15

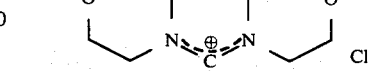 Compound 16

Compound 17

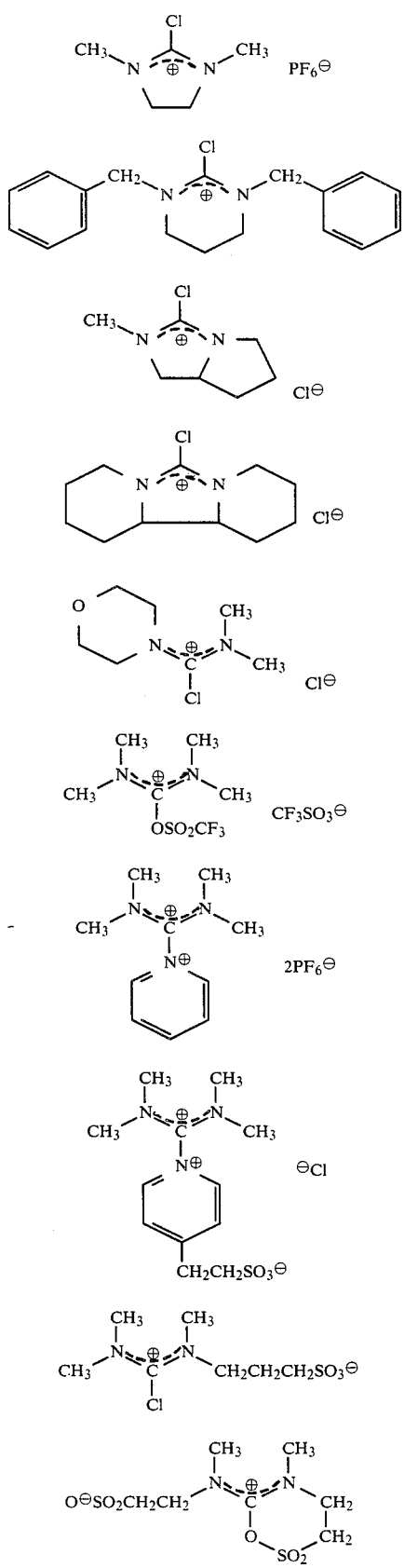

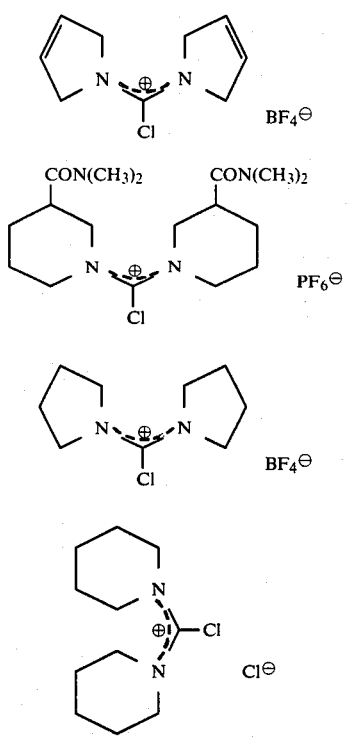

Compound 36

Compound 37

Compound 38

Compound 39

Then, practical synthesis examples of the compounds of this invention are shown below.

SYNTHESIS EXAMPLE 1

(Synthesis of Compound 1)

To a 1,2-dichloroethane (30 ml) solution of 11.6 g of N,N,N',N'-tetramethylurea was added dropwise a 1,2-dichloroethane (10 ml) solution of 10 ml of oxalyl chloride at room temperature over a period of 10 minutes, and after stirring the mixture for 3 hours at 40° C., the reaction mixtue thus formed was allowed to cool to deposit crystals. The crystals were collected by filtration, washed with a small amount of 1,2-dichloroethane, and dried to provide Compound 1 as hygroscopic crystals. The melting point thereof was 135° to 140° C. and the yield was 12.1 g. The chemical structure of the product as confirmed by the nuclear magnetic resonance spectra, infrared absorption spectra, and the elemental analysis.

SYNTHESIS EXAMPLE 2

(Synthesis of Compound 4)

Compound 1 (17.1 g) obtained in Synthesis Example 1 was dissolved in a small amount of cold water and then an aqueous solution ($H_2O$: 40 ml) of 20 g of $NH_4PF_6$ was added to the solution. Crystals thus deposited were collected by filtration, dried after washing with water, and recrystallized from 1,2-dichloroethane to provide Compound 4. Compound 4 could be sparingly soluble in water but could be easily soluble in water containing a small amount of acetone. The melting point thereof was 98° to 98.5° C. and the yield was 25.3 g. The chemical structure was confirmed by the nuclear magnetic resonance spectra, infrared absorption spectra, and elemental analysis.

SYNTHESIS EXAMPLE 3

(Synthesis of Compound 16)

To a 1,2-dichloroethane (50 ml) solution of 20.1 g of N,N'-carbonyldimorpholine was gradually added a 1,2-dichloroethane (10 ml) solution of 10 ml of oxalyl chloride, and after stirring the mixture for 3 hours at 60° C., the volatile matters were distilled off under reduced pressure. The residue was washed with ether and further recrystallized from 1,2-dichloroethane to provide Compound 16. The melting point thereof was 115° to 118° C. and the yield was 15.4 g. The chemical structure of the product was confirmed by the nuclear magnetic resonance spectra, infrated absorption spectra, and elemental analysis.

SYNTHESIS EXAMPLE 4

(Synthesis of Compound 18)

To a 1,2-dichloroethane (50 ml) solution of 11.4 g of 1,3-dimethyl-2-imidazolidone was gradually added a 1,2-dichloroethane (10 ml) solution of 10 ml of oxalyl chloride, and after stirring the mixture for 4 hours at 60° C., the volatile matters were distilled off under reduced pressure. The residue thus formed was dissolved in cold water and then an aqueous solution ($H_2O$: 40 ml) of 20 g of $NH_4PF_6$ was added to the solution. Crystals thus formed were collected by filtration, washed with water, dried, and recrystallized from 1,2-dichloroethane to provide Compound 18. The melting point thereof was 233° to 234° C. and the yield thereof was 10.4 g. The chemical structure of the product was confirmed by the nuclear magnetic resonance spectra, infrared absorption spectra, and elemental analysis.

SYNTHESIS EXAMPLE 5

(Synthesis of Compound 14)

To a 1,2-dichloroethane (50 ml) solution of 7 g of N,N'-carbonyldipyrrolidine was dropwise added a 1,2-dichloroethane (10 ml) solution of 10 ml of oxalyl chloride at 40° C. over a period of 10 minutes and after stirring the mixture for 3 hours at 50° C., the volatile matters were distilled off under reduced pressure. The residue was washed with ether repeatedly to crystallize the product. After drying the product, Compound 14 was obtained. The yield was 6.4 g. The chemical structure of the product was confirmed by the nuclear magnetic resonance spectra, infrared absorption spectra, and elemental analysis.

SYNTHESIS EXAMPLE 6

(Synthesis of Compound 30)

To a methylene chloride (20 ml) solution of 2.7 g of Compound 14 was added 3 g of sodium 2-naphthalene sulfonate, followed by stirred for 1 hour at 30° C. After the solid thus obtained was removed by filtation, acetone was added to the filtrate. Crystals thus obtained were collected by filtration to obtain Compound 30. The melting point thereof was 142° to 144° C. and the yield was 2.2 g. The chemical structure of the product was confirmed by the nuclear magnetic resonance spectra, infrared absorption spectra, and the elemental analysis.

SYNTHESIS EXAMPLE 7

(Synthesis of Compound 39)

To a 1,2-dichloroethane (100 ml) solution of 19.6 g N,N'-carbonyldipiperazine was dropwise added 10 ml of oxalyl chloride at 40° C. over a period of 10 minutes, and after stirring the mixture for 4 hours at that temperature, the volatile matters were distilled off under reduced pressure. The residue was washed with ether repeatedly to crystallize the product. After drying, the product Compound 39 was obtained. The yield was 30.5 g. The chemical structure of the product was confirmed by the nuclear resonance spectra, infrared absorption spectra, and the elemental analysis.

SYNTHESIS EXAMPLE 8

(Synthesis of Compound 31)

To a 1,2-dichloroethane (300 ml) solution of 36.3 g of Compound 39 was added 31.5 g of $NH_4BF_4$ and stirred for 1 hour at room temperature. After removing the solid thus obtained by filtration, the solvent was distilled off under reduced pressure. The residue was washed with ether and dried to obtain Compound 31. The melting point was 65° to 67° C. and the yield was 36.5 g. The chemical structure of the product was confirmed by the nuclear magnetic resonance spectra, infrared absorption spectra, and the elemental analysis.

Other compounds of this invention represented by formula (I) can also be prepared by the methods similar to the above-described methods.

When these compounds are applied to gelatin-containing silver halide photographic layers as hardening agents, the occurrence of undesirable phenomena such as the formation of fog, reductions in photographic properties, such as desensitization, etc., the formation of stain, the reaction with couplers contained in the color photographic materials, etc., is scarcely observed. Also, the progress of layer hardening is very quick to reach the state of the final hardened layer within a few days after coating the layer, and a post hardening phenomenon, i.e., a phenomenon wherein the hardness of the hardened layer increases thereafter, is not substantially observed.

These compounds are excellent in affinity with water, require no specific organic solvent in the case of adding to an aqueous emulsion, and hence uneven coating caused by organic solvent does not occur. Also, in the case of using the above-described compounds, it is not necessary to take steps for the prevention of the occurrence of explosions caused by the use of an organic solvent. Furthermore, these compounds do not have specific physiological action, and have little adverse influence on the human body since the vapor pressure thereof is low.

The amount of the hardening agent for use in this invention can be optionally selected according to the intended purpose, but is usually in the range of from 0.01 to 20% by weight to dry gelatin, and more preferably 0.05 to 10% by weight to dry gelatin.

The hardening agent for use in this invention can be effectively used as a hardening agent for partial hardening in the method of prolonging the chain length of gelatin by partial hardening thereof as described in Japanese Patent Application (OPI) No. 2324/'81, corresponding to U.S. Pat. No. 4,421,847. Furthermore, the compound can be used for hardening the chain-prolonged gelatin.

The hardening agents in this invention can be used, for every photographic materials using gelatin, such as color photographic materials, for example, color photographic negative films, color photographic reversal films, color photographic positive films, color photographic papers, color photographic reversal papers, color photographic materials for color diffusion transfer system and silver dye bleach system, black and white photographic materials, for example, black and white photographic films, radiographic photographic films, lithographic film, black and white photographic papers, aviation photographic films, micrographic film, facsimile recording films, typesetting films and papers, graphic photographic films, etc.

Also, in this case, there is no particular restriction on the photographic layers using the hardening agent of this invention and the hardening agent can be used for not only silver halide emulsion layers but also non-sensitive layers such as subbing layers, backing layers, filter layers, interlayers, overcoat layers, etc., containing gelatin.

The hardening agents in this invention can be used singly or as a mixture thereof. Also, the hardening agents may be used together with conventionally known hardening agents. Examples of these known hardening agents are aldehyde series compounds such as formaldehyde, glutaraldehyde, etc.; ketone compounds such as diacetyl and cyclopentanedione, etc.; bis(2-chloroethylurea); 2-hydroxy-4,6-dichloro-1,3,5-triazine; as well as the compounds having reactive halogens described in U.S. Pat. Nos. 3,288,775; 2,732,303; U.K. Pat. Nos. 974,723; 1,167,207, etc.; divinylsulfone; 5-acetyl-1,3-diacryloylhexahydro-1,3,5-triazine; the compounds having reactive olefin described in U.S. Pat. Nos. 3,635,718; 3,232,763; 3,539,644; U.K. Pat. No. 99,869; Japanese Patent Application (OPI) Nos. 41,221/'78; 57257/'78; Japanese Patent Publication No. 13,563/'74; *Research Disclosure*, No. 17,458, etc.; N-hydroxymethyl phthalimide; the N-methylol compounds described in U.S. Pat. Nos. 2,532,316; 2,586,168, etc.; the isocyanates described in U.S. Pat. No. 3,103,437; the aziridine compounds described in U.S. Pat. Nos. 3,017,280; 2,983,611, etc.; the acid derivatives described in U.S. Pat. Nos. 2,725,294; 2,725,295, etc.; the carbodiimide series compounds described in U.S. Pat. No. 3,100,704, etc.; the epoxy compounds described in U.S. Pat. No. 3,091,537, etc.; the isooxazole series compounds described in U.S. Pat. Nos. 3,321,313; 3,543,292, etc.; halogenocarboxyaldehydes such as mucochloric acid, etc.; dioxanes such as dihydroxydioxane, dichlorodioxane, etc.; dihydroquinoline compounds; compounds having a phosphorus-halogen bond; N-sulfonyloxyimide series compounds; N-acyloxyimino series compounds; the N-carbonyloxyimide series compounds described in Japanese Patent Application (OPI) No. 43,353/'81; 2-sulfonyloxypyridinium salts; N-carbamoylpyridinium salts, etc.

Furthermore, inorganic hardening agents such as chromium alum, zirconium sulfate, etc., may be used together with the hardening agents for use in this invention.

Also, in place of the aforesaid compounds, precursor-form compounds, such as, for example, alkali metal bisulfite aldehyde addition products, methylol derivatives of hydantoin; primary aliphatic nitroalcohols, mesyloxyethylsulfonyl series compounds, chloroethylsulfonyl series compounds, etc., may be used.

In the case of using the hardening agent of this invention together with other hardening agents as described above, the proportion of the hardening agent of this invention may be desirably selected according to the purpose and effect thereof but is preferably higher than 50 mole%.

A compound capable of accelerating hardening of gelatin may be used together with the hardening agent for use in this invention. Examples of such a hardening accelerating agent are the nonprotonic solvents described in West German Patent Application (OLS) No. 2,417,586; the betaine type surface active agents described in Japanese Patent Application (OPI) No. 62,045/'82; tertiary amines and the salts thereof as described in Japanese Patent Application (OPI) Nos. 1043/'81; 9434/'81; West German Patent Application (OLS) No. 2,138,305; U.K. Pat. Nos. 1,284,305; 1,269,983, etc., and various inorganic salts and polyhydric alcohols. These accelerating hardening agents may be used together with the hardening agent of the present invention and the above-described conventional hardening agent. For example, the system of using the hardening agent in this invention and a vinylsylfone series hardening agent is used together with the polymer containing sulfinic acid group described in Japanese Patent Application (OPI) No. 4141/'81 as a hardening accelerator.

As gelatin to which the hardening agent of this invention is applied, there are so-called alkali-treated gelatin (limed gelatin) immersed in an alkali bath before gelatin extraction, acid-treated gelatin immersed in an acid bath, gelatin treated by double-immersing in an alkali and an acid, and enzyme-treated gelatin described in *Bull. Soc. Sci. Photo. Japan*, No. 16, 30(1966). Furthermore, the hardening agent of this invention can be applied to partially hydrolyzed low molecular weight gelatin prepared by heating the aforesaid gelatin in a water bath or reacting the gelatin with proteolytic enzyme.

The gelatin to which the hardening agent of this invention is applied can be, if desired, partially replaced with a cellulose derivative such as colloidal albumin, casein, carboxymethyl cellulose, hydroxyethyl cellulose, etc.; a sugar derivative such as agar agar, sodium alginate, starch derivatives, etc.; synthetic hydrophilic colloid such as polyvinyl alcohol, poly-N-vinylpyrrolidone, a polyacrylic acid copolymer, polyacrylamide, derivatives thereof, the partially hydrolyzed products of them, etc. Furthermore, gelatin may be partially replaced with a so-called gelatin derivative prepared by treating and reforming the amino group, imino group, hydroxy group, and carboxy group contained in the molecule as functional groups with a reagent having a group capable of reacting with these groups or a graft polymer of gelatin prepared by connecting gelatin with the molecular chain of other high molecular weight material.

Examples of reagents for forming the aforesaid gelatin derivatives include isocyanates, acid chlorides, and acid anhydrides described, for example, in U.S. Pat. No. 2,614,928; the acid anhydrides described in U.S. Pat No. 3,118,766; the bromoacetic acids described in Japanese Patent Publication No. 5514/'64; the phenylglycidyl ethers described in Japanese Patent Publication No. 26,845/'67; the vinylsulfone compounds described in U.S. Pat. No. 3,132,945; the N-allylvinylsulfoneamides described in U.K. Pat. No. 861,414; the maleimide compounds described in U.S. Pat. No. 3,186,846; the acrylonitriles described in U.S. Pat. No. 2,594,293; the polyalkylene oxides described in U.S. Pat. No. 3,312,553; the epoxy compounds described in Japanese Patent Publication No. 26,845/'67; the acid esters described in U.S. Pat. No. 2,763,639; and the alkanesultones described in U.K. Pat. No. 1,033,189.

Also, the branched high molecular weight material which is grafted to gelatin to form the aforesaid graft polymer of gelatin are described in U.S. Pat. Nos. 2,763,625, 2,831,767, and 2,956,884; *Polymer Letters*, Vol. 5, 595(1967); *Phot. Sci. Eng.*, Vol. 9, 148(1965); *J. Polymer Sci.*, A-1, Vol. 9, 3199(1971), etc., and polymers or copolymers of vinyl monomers such as acrylic acid, methacrylic acid, the derivatives thereof, such as the esters, amides and nitriles, styrene, etc., can be widely used as the branched high molecular weight materials. However, hydrophilic vinyl polymers having a compatibility with gelatin to some extent, such as the polymers or copolymers of acrylic acid, acrylamide, methacrylamide, hydroxyalkyl acrylate, hydroxyalkyl methacrylate, etc., are particularly preferred.

In the case of using the hardening agent of this invention for photographic materials, the silver halide emulsion layers and other layers of the photographic materials may contain synthetic polymers such as latex-like water-dispersed vinyl compound polymers. In particular, compounds capable of increasing the dimensional stability of the photographic materials singly or as a mixture thereof, or further in combination thereof with a hydrophilic water permeable colloid.

In the case of using the gelatin hardening agent of this invention for photographic materials, the hardening agent may be used with a matting agent. The matting agent is fine particles of a water-insoluble organic or inorganic compound having a mean particle size of from 0.2 $\mu$m to 10 $\mu$m, and preferably from 0.3 $\mu$m to 5 $\mu$m.

Furthermore, in the case of using the hardening agent of this invention for photographic materials, the photographic materials may contain dye-forming couplers, i.e., yellow couplers, magenta couplers, and cyan couplers.

Typical examples of the yellow coupler are described in U.S. Pat. Nos. 2,875,057, 2,407,210, 3,265,506, 2,298,443, 3,048,194, 3,447,928, etc. Of these yellow couplers, acylacetamide derivatives such as benzoylacetanilide, pivaloylacetanilide, etc., are preferred.

Typical examples of the magenta couplers are described in U.S. Pat. Nos. 2,600,788, 2,369,489, 2,343,703, 2,311,082, 3,152,896, 3,519,429, 3,062,653, 2,908,573, 3,725,067; U.K. Pat. No. 1,047,612, etc. In these magenta couplers, 5-pyrazolones and pyrazoloazoles (e.g., pyrazolopyrazole, pyrazoloimidazole, pyrazolotriazole, pyrazolotetrazole, etc.) are preferred.

Typical examples of the cyan couplers are described in U.S. Pat. Nos. 2,772,162, 2,895,826, 3,002,836, 3,034,892, 2,474,293, 2,423,730, 2,367,531, 3,041,236, etc. In these cyan couplers, phenols, or naphthols are preferred. In these couplers, the cyan couplers forming dyes having improved fastness are described, for example, in Japanese Patent Publication No. 37,857/'82; Japanese Patent Application (OPI) Nos. 80,045/'81, 31,953/'84, 31,954/'84, etc.

The compounds having an ethylenically polymerizable group at other portion than the coupling position of the above-described yellow couplers, magenta couplers, or cyan couplers may be used solely or as a mixture thereof, or, if desired, so-called polymer couplers having a repeating unit of non-coloring monomer may be used.

In the case of using the hardening agent of this invention for photographic materials, couplers may be introduced in silver halide emulsion layers by known method described in U.S. Pat. No. 2,322,027, etc. For example, the coupler is dissolved in a high-boiling organic solvent such as a phthalic acid alkyl ester (e.g., dibutyl phthalate, dioctyl phthalate, etc.), a phosphoric acid ester (e.g., diphenyl phosphate, triphenyl phosphate, tricresyl phosphate, dioctylbutyl phosphate, etc.), a citric acid ester (e.g., tributyl acetylcitrate, etc.), a benzoic acid ester (e.g., octyl benzoate, etc.), an alkylamide (e.g., diethyllaurylamide, etc.), a fatty acid ester (e.g., dibutoxyethyl succinate, diethyl azelate, etc.), a trimesic acid ester (e.g., tributyl trimesate, etc.), etc., or a low-boiling organic solvent having a boiling point of about 30° to 150° C., such as a lower alkyl acetate (e.g., ethyl acetate, butyl acetate, etc.), ethyl propionate, secondary butyl alcohol, methyl isobutyl ketone, β-ethoxyethyl acetate, methylcellosolve acetate, etc., and then dispersed in an aqueous hydrophilic colloid solution as the organic solvent solution. The above-described high-boiling organic solvent and low-boiling organic solvent may be used as a mixture thereof.

Also, a dispersing method by polymers described in Japanese Patent Publication No. 39,853/'76 and Japanese Patent Application (OPI) No. 59,943/'76 may be used for incorporating the couplers in the photographic emulsion layers.

When the coupler has an acid group such as a carboxylic acid group or a sulfonic acid group, the compound is introduced into an aqueous hydrophilic colloid solution as an alkaline aqueous solution thereof.

In the case of using a polymer coupler, the polymer coupler may be prepared by an emulsion polymerization or a solution polymerization. In the emulsion polymerization, the polymerized product may be added as it is to a silver halide emulsion. In the solution polymerization, the polymerized product may be once removed from the polymerization system, dissolved in an organic solvent, and dispersed in a silver halide emulsion as the organic solvent solution.

In the case of using the hardening agent of this invention for photographic materials, the silver halide for silver halide photographic emulsion layers may be silver bromide, silver iodobromide, silver iodochlorobromide, silver chlorobromide, or silver chloride.

There is no particular restriction on the mean grain size of silver halide grains in the silver halide photographic emulsion (when the silver halide grains are spherical or similar to spherical form, the mean grain size is shown by the mean diameter of the grains and when the silver halide grains are cubic grains, the edge length is taken as the grain size and the mean grain size is shown by the mean value based on the projected area) but the mean grain size is preferably less than 3 μm.

The distribution of the grain size may be narrow or broad.

The silver halide grains in the photographic emulsions using the hardening agent of this invention may have a regular crystal form such as cubic or octahedral, or may have an irregular crystal form such as a spherical form or a tabular form, or may be a composite form of these crystal forms. Furthermore, the silver halide grains may be composed of a mixture of plural silver halide grains having different crystal forms.

Also, a silver halide emulsion wherein silver halide grains of a tabular form having a diameter of the grain more than 5 times longer than the thickness thereof occupy more than 50% of the whole projected area may be used.

The silver halide grains may differ in phase between the surface layer and the inside thereof. Also, the silver halide grains may be grains forming a latent image mainly on the surface or may be grains forming a latent image mainly in the inside thereof.

The silver halide emulsions to which the hardening agent of this invention is applied can be prepared by using the methods as described, for example, in P. Glafkides, *Photographique* (published by Paul Montel, 1967), G. F. Duffin, *Photographic Emulsion Chemistry*, (published by The Focal Press, 1966), V. L. Zelikman et al, *Making and Coating Photographic Emulsion*, (published by The Focal Press, 1964).

That is, the emulsion may be prepared by an acid method, a neutralization method, an ammonia method, etc., and a soluble silver salt and a soluble halide may be reacted by a one-side mixing method, a simultaneous mixing method, or a combination of these methods.

Furthermore, a so-called back mixing method for forming silver halide grains in the presence or excessive silver ion can be used for preparing the silver halide emulsion. Also, as on system of the simultaneous mixing method, a so-called controlled double jet method for maintaining the pAg value of the liquid phase forming silver halide at a constant value can be used. According to this method, a silver halide emulsion wherein the crystal form of the silver halide grains is regular and the grain sizes are almost uniform is obtained.

A mixture of two or more silver halide emulsions formed separately may be used.

The silver halide grains may be formed or physically ripened in the presence of a cadmium salt, a zinc salt, a lead salt, a thallium salt, an iridium salt, or a complex salt thereof, a rhodium salt or a complex salt thereof, an iron salt or a complex salt thereof, etc.

After forming the precipitation of the silver halide emulsion or after physical ripening of the silver halide emulsion, soluble salts are usually removed from the emulsion. The removal of the soluble salts may be performed by the well-known noodle washing method of washing the emulsion with water after gelling, or may be performed by using a flocculation method utilizing an inorganic salt composed of a polyvalent anion.

The silver halide emulsion using the hardening agent of this invention are usually chemically sensitized. For the chemical sensitization, the method described, for example, in H. Frieser, *Die Grundlagen der Photographischen Prozesse mit Silberhalogeniden*, published by Akademische Verlagsgesellschaft, 1968, pages 675–734, can be used.

Examples thereof include a sulfur sensitizing method using active gelatin or a compound containing sulfur capable of reacting with silver (e.g., thiosulfates, thioureas, mercapto compounds, rhodanines, etc.), a reduction sensitizing method using a reducing material (e.g., stannous salts, amines, hydrazine derivatives, formamidinesulfinic acid, silane compounds, etc.), a noble metal sensitizing method using a noble metal compound (e.g., gold complex salts and complex salts of metals belonging to group VIII of the periodic table, such as platinum, iridium, palladium, etc.). They can be used individually or as a combination thereof.

The silver halide photographic emulsions to which the hardening agents of this invention are applied may further contain various compounds for preventing the formation of fog during the production and storage of the photographic materials containing the emulsions or stabilizing the photographic performance of the photographic materials. Examples include antifoggants and stabilizers as azoles (e.g., benzothiazolium salts, nitroimidazoles, nitrobenzimidazoles, chlorobenzimidazoles, bromobenzimidazoles, mercapto-thiazoles, mercaptobenzothiazoles, mercaptobenzimidazoles, mercaptothiadiazoles, aminotriazoles, benzotriazoles, nitrobenzotriazoles, mercaptotetrazoles (in particular, 1-phenyl-5-mercaptotetrazole), etc.; mercaptopyrimidines; mercaptotriazines; thioketo compounds (e.g., oxadolinethione, etc.); azaindenes (e.g., triazaindenes, tetraazaindenes (in particular, 4-hydroxy-substituted (1,3,3a,7)tetraazaindenes), pentaazaindenes, etc.); benzenethiosulfonic acid, benzenesulfinic acid; benzenesulfonic acid amide, etc.

The photographic materials using the hardening agents of this invention can further contain various surface active agents in the silver halide photographic emulsion layers or other hydrophilic colloid layers for improving coating property, antistatic property, slidability, emulsifying property, adhesion resistance, and photographic properties (e.g., development acceleration, and the increase of contrast and sensitivity).

Also, the silver halide photographic emulsion layers of the photographic material of this invention may contain polyalkylene oxide or derivatives thereof such as the ethers, esters, amines, etc., thereof, thioether compounds, thiomorpholines, quaternary ammonium salt compounds, urethane derivatives, urea derivatives, imidazole derivatives, 3-pyrazolidones, etc., for the purposes of sensitivity increase, contrast increase, or development acceleration.

Furthermore, the photographic materials to which the hardening agents of this invention are applied may further contain a dispersion of a water-insoluble or water sparingly soluble synthetic polymer in the silver halide photographic emulsion layers and other hydrophilic colloid layers for improving the dimensional stability, etc. As the synthetic polymer, a polymer or copolymer of alkyl (meth)acrylate, alkoxyalkyl(meth)acrylate, glycidyl (meth)acrylate, (meth)acrylamide, a vinylester (e.g., vinyl acetate), acrylonitrile, olefins, styrene, etc., singly or as a combination thereof, or as a combination of the monomer and acrylic acid, methacrylic acid, $\alpha,\beta$-unsaturated dicarboxylic acid, hydroxyalkyl(meth)acrylate, sulfoalkyl(meth)acrylate, styrenesulfonic acid, etc., can be used.

The silver halide photographic emulsions used in this invention may be spectrally sensitized by methine dyes, etc. Examples of the dyes for the spectral sensitization include cyanine dyes, merocyanine dyes, complex cyanine dyes, complex merocyanine dyes, holopolar cyanine dyes, hemicyanine dyes, styryl dyes, and hemioxonole dyes. Particularly useful dyes are cyanine dyes, merocyanine dyes, and complex merocyanine dyes. For these dyes, nuclei usually utilized for cyanine dyes, such as basic heterocyclic nuclei can be used. Examples of such nuclei include a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc.; nuclei formed by fusing an alicyclic hydrocarbon ring to these nuclei as described above and nuclei formed by fusing an aromatic hydrocarbon ring to these nuclei, such as an indolenine nucleus, a benzindolenine nucleus, an indole nucleus, a benzoxadole nucleus, a naphthoxazole nucleus, a benzothiazole nucleus, a naphthothiazole nucleus, a benzoselenazole nucleus, a benzimidazole nucleus, a quinoline nucleus, etc. these nuclei may be substituted on carbon atoms.

For the merocyanine dyes or complex merocyanine dyes may be applied a 5 to 6 membered heterocyclic nucleus such as a pyrazolin-5-one nucleus, a thiohydantoin nucleus, a 2-thiooxazolidine-2,4-dione nucleus, a thiazolidine-2,4-dione nucleus, a rhodanine nucleus, a thiobarbituric acid nucleus, etc., as a nucleus having a ketomethylene structure.

These sensitizing dyes may be used individually and also as combinations thereof. In particular, a combination of sensitizing dyes can be frequently used for the purpose of supersensitization.

The silver halide photographic emulsion used in this invention is applied may further contain a dye having no spectral sensitization action by itself, or a material which does not substantially absorb visible light, but which shows a super sensitizing action when used together with the aforesaid sensitizing dye or dyes. Examples of such material are aminostyryl compounds substituted by a nitrogen-containing heterocyclic ring group (as described, e.g., in U.S. Pat. Nos. 2,933,390; 3,635,721, etc.), aromatic organic acid-formaldehyde condensation products (as described, e.g., in U.S. Pat. No. 3,743,510, etc.), cadmium salts, azaindene compounds, etc.

This invention can be applied for multilayer multicolor photographic materials having two or more photographic emulsion layers of different spectral sensitivities on a support. A multilayer natural color photographic material usually has on a support at least one red-sensitive emulsion layer, at least one green-sensitive emulsion layer, and at least one blue-sensitive emulsion layer. The disposition order of these layers may be optionally selected according to the intended purpose.

It is usual that the red-sensitive emulsion layer contains a cyan-forming coupler, the green-sensitive emulsion layer contains a magenta-forming coupler, and the blue-sensitive emulsion layer contains a yellow-forming coupler, but other combinations can be employed if desired.

When the hydrophilic colloid layers of the photographic materials for which the hardening agents of this invention are applied contain a dye or a ultraviolet absorbent, the dye or absorbent may be mordanted by a cationic polymer.

The photographic materials to which the hardening agents of this invention are applied may further contain hydroquinone derivatives, aminophenol derivatives, gallic acid derivatives, ascorbic acid derivatives, etc., as a color fog preventing agent.

Furthermore, the photographic materials to which the hardening agents of this invention are applied may contain ultraviolet absorbents in the hydrophilic colloid layers. Examples of the ultraviolet absorbents are benzotriazole compounds substituted by an aryl group (as described, for example, in U.S. Pat. No. 3,533,794, etc.), 4-thiazolidone compounds (as described, for example, in U.S. Pat. Nos. 3,314,794, 3,352,681, etc.), benzophenone compounds (as described, for example, in Japanese Patent Application (OPI) No. 2784/'71), cinnamic acid ester compounds (as described, for example, in U.S. Pat. Nos. 3,705,805; 3,707,375, etc.), and butadiene compounds (as described, for example, in U.S. Pat. No. 4,045,229). Ultraviolet absorbing couplers (e.g., α-naphtholic cyan-forming couplers) or ultraviolet absorbing polymers may be used.

The photographic materials to which the hardening agents of this invention are applied may further contain in the hydrophilic colloid layers water-soluble dyes as filter dyes or for the purposes of irradiation prevention and others. These dyes include oxonole dyes, hemioxonole dyes, styryl dyes, merocyanine dyes, cyanine dyes, and azo dyes. Among these dyes, oxonole dyes, hemioxonole dyes, and merocyanine dyes are useful.

The photographic materials to which the hardening agents of this invention are applied may further contain following known fading preventing agents or dye image stabilizers, which may be used singly or as a mixture thereof. Examples of the fading preventing agent are hydroquinone derivatives described in, for example, Japanese Patent Application (OPI) No. 10,539/'84, gallic acid derivatives, p-alkoxyphenols, p-oxyphenol derivatives, and bisphenols.

The silver halide photographic emulsions used in this invention each is coated on a flat material causing no severe dimensional change during photographic processing, such as a hard support, e.g., a glass plate, a metal plate, a porcelain, etc., or a flexible support.

Typical flexible supports for photographic materials include cellulose acetate films, polyethylene terephthalate films, polycarbonate films, laminates of these films, baryta-coated papers, and papers coated or laminated with an α-olefin polymer, in particular, a polymer of an α-olefin having 2 to 10 carbon atoms, such as polyethylene, polypropylene, etc.

The photographic silver halide emulsion layers hardened using the hardening agent of this invention can be processed by any known photographic processing processes, and known processing solutions, as described, e.g., in *Research Disclosure,* No. 176, pages 28-30. The processing temperature is usually selected in the range of from 18° C. to 50° C., but may be lower than 18° C. or higher than 50° C.

A fixing solution having a generally employed composition may be used. As the fixing agent, a thiosulfate, a thiocyanate, and organic sulfur compounds which are known to having an effect as a fixing agent can be used. The fix solution may contain a water-soluble aluminum salt as a hardening agent.

A color developer which can be used for developing the color photographic materials the photographic layers of which are hardened by the hardening agents of this invention is compoosed of an alkaline aqueous solution containing a color developing agent. As the color developing agent, a known primary aromatic amine developing agent such as phenylenediamines (e.g., 4-amino-N,N-diethylaniline, 3-methyl-4-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methane-sulfonamidoethylaniline, 4-amino-3-methyl-N-ethyl-N-β-methoxyethylaniline, etc.) can be used.

Furthermore, color developing agents described, for example, in L. F. A. Mason, *Photographic Processing Chemistry,* pages 226-229 (published by The Focal Press, 1966); U.S. Pat. Nos. 2,193,015 and 2,592,364; Japanese Patent Application (OPI) No. 64,933/'73, etc., can be also used.

The color developer may further contain a pH buffer such as a sulfite, carbonate, borate, or phosphate of an alkali metal, a development inhibitor or an antifoggant such as a bromide, an iodide, and an organic antifoggant. Also, if necessary, the color developer may further contain a water softener, a preservative such as hydroxylamine, etc., an organic solvent such as benzyl alcohol, diethylene glycol, etc., a development accelerator such as polyethylene glycol, a quaternary ammonium salt, an amine, etc., a dye-forming coupler, a competing coupler, a fogging agent such as sodium boron hydride, etc., an auxiliary developing agent such as 1-phenyl-3-pyrazolidone, etc., a tackifier, a polycarboxylic acid series chelating agent, an anti-oxidant, etc.

The silver halide photographic emulsion layers are usually bleached after color development. The bleach process may be performed simultaneously with a fix process or separately from the fix process. As the fixing agent, compounds of polyvalent metals such as iron(III), cobalt(III), chromium(IV), copper(II), etc., peroxides, quinones, nitroso compounds, etc., can be used.

Examples of the bleaching agent are ferricyanides; dichromates; organic complex salts of iron(III) or cobalt(III); complex salts of aminopolycarboxylic acids such as ethylenediaminetetraacetic acid, nitrilotriacetic acid, 1,3-diamino-2-propanoltetraacetic acid, etc., or complex salts of organic acids such as citric acid, tartaric acid, malic acid, etc.; a persulfate, a permanganate; nitrosophenol, etc. Among these materials, potassium ferricyanide, ethylenediaminetetraacetic acid iron(III) sodium, and ethylenediaminetetraacetic acid iron(III) ammonium are particularly useful. The ethylenediaminetetraacetic acid iron(III) complex salt is useful in a bleach solution and a blix solution.

The gelatin hardening method of this invention can be used not only for photographic materials, but also can be applied to other fields of using gelatin by hardening.

For example, the invention can be applied for hardening microcapsules as described, for example, in U.S. Pat. No. 4,016,098.

The invention is further described by the following examples, but the invention is not limited to these examples.

EXAMPLE 1

After adding Compounds 1, 14, 30 and 31, in this invention, Comparison compound (IV) disclosed in Japanese Patent Application (OPI) No. 59,625/'76 (as illustrated compound 15), or Comparison compound (V) disclosed in U.S. Pat. No. 3,642,486 (in Example II) to an aqueous 7% gelatin solution at a ratio as shown in Table 1, the mixture was uniformly coated on a cellulose triacetate support at a dry thickness of about 8 μm and dried to provide each of gelatin layers (A) to (G). Also, a gelatin layer (H) containing no hardening agent was prepared as a control sample.

Each sample was placed under the conditions of 25° C. and 50% in relative humidity, and after 2 hours, one day, 3 days, or 7 days since the coating, each sample was measured with respect to the crosslinking coefficient δ (i.e., the crosslinked unit number per the weight mean molecular weight of gelatin before crosslinking) by the following method.

That is, each gelatin layer was separated from the support and the weight $M_1$ thereof was measured. From each gelatin layer, the sol components were extracted with hot water and the gelatin weight $M_2$ thereof was measured by a microburette method. From these results, a sol content S was determined according to the following equation;

$$S = M_2/M_1$$

From the value S thus obtained, δ was calculated according to the following equation described in A. Cherlersby, *Atomic Radiation and Polymers*, pages 134–158, published by Pergamon Press, 1960;

$$\delta = \frac{2}{S + \sqrt{S}}$$

The values of δ of gelatin layers (A) to (H) in each measured time are shown in Table 1 below.

TABLE 1

| Gelatin Layer | Hardening Agent | Addition Amount per 100 g of gelatin | δ 2 hours | 1 day | 3 days | 7 days |
|---|---|---|---|---|---|---|
| (A) | Compound 1 of Invention | 5 m mol | 2.1 | 2.0 | 1.9 | 2.0 |
| (B) | " | 10 m mol | 3.9 | 3.7 | 3.8 | 3.8 |
| (C) | " | 20 m mol | 6.1 | 6.1 | 6.0 | 6.1 |
| (D) | Compound 14 of Invention | 10 m mol | 3.9 | 4.2 | 4.1 | 4.2 |
| (E) | " | 20 m mol | 6.5 | 6.8 | 7.0 | 7.0 |
| (F) | Compound 30 of Invention | 10 m mol | 4.0 | 4.1 | 4.2 | 4.2 |
| (G) | " | 20 m mol | 6.6 | 7.0 | 7.1 | 7.0 |
| (H) | Compound 31 of Invention | 10 m mol | 4.4 | 4.3 | 4.3 | 4.3 |
| (I) | " | 20 m mol | 7.1 | 6.8 | 7.0 | 7.0 |
| (J) | Comparison compound (IV) | 5 m mol | 1.5 | 1.6 | 1.5 | 1.6 |
| (K) | " | 10 m mol | 2.8 | 2.7 | 2.7 | 2.8 |
| (L) | " | 20 m mol | 4.5 | 4.3 | 4.4 | 4.4 |
| (M) | Comparison compound (V) | 5 m mol | 1.2 | 3.4 | 5.6 | 6.4 |
| (N) | none | 0 | 1.0 | 1.0 | 1.0 | 1.0 |

Comparison compound (IV)

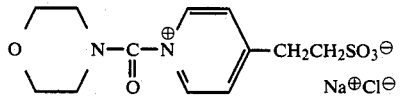

Comparison compound (V)

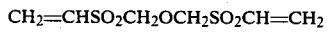

From the results shown in Table 1, it can be seen that gelatin layers (A) to (I) using Compounds 1, 14, 30, and 31 of this invention show fast hardening action and the hardening reaction is complete in about 2 hours after the coating, and δ does not change thereafter.

On the other hand, in the case of using Comparison compound (IV), the result was the same as the case of using Compound 1 in the point of fast hardening action, but by a poor selectivity for the reaction with the reactive residue in the gelatin, the crosslinking coefficient was only about 75% of the system using the same amount of Compound 1 (comparison of gelatin layer (A) and gelatin layer (J), gelatin layer (B) and gelatin layer (K), or gelating layer (C) and gelatin layer (L)) and hence the effective using efficiency as hardening agent is low. Also, in the case of using Comparison compound (V), the hardening action was slow and was increased further after 3 days (i.e., post hardening occurred).

From the above results, it is clear that Compounds 1, 14, 30, and 31 of this invention show a fast hardening action and is a hardening agent having excellent using efficiency.

EXAMPLE 2

To a high-speed negative working silver halide photographic emulsion containing 120 g of gelatin and 65 g of silver iodobromide per 1 g of silver halide emulsion prepared according to an ordinary method Compound 1 of this invention or Comparison compound (V) as shown in Table 2 below and each silver halide emulsion was uniformly coated on a cellulose triacetate support having a subbing layer at a dry thickness of 10 μm and dried to provide each sample. Each sample was allowed to stand for 7 days at room temperature and then the swelling degree Q shown by the following equation was measured in water at 25° C.

$$Q = \frac{\text{Increased layer thickness by swelling}}{\text{Layer thickness upon drying}}$$

Also, each sample was immersed in water, a stylus having a steel ball of 0.4 mm radius at the tip thereof was brought into contact with the sample surface, while moving the steel ball on the surface at a speed of 2.5 mm/sec in parallel with the surface, a load applied to the stylus was continuously changed in the range of 0 to 200 g, and the load of the stylus causing scratches on the layer surface of each sample was determined.

Furthermore, each film sample obtained was wedge-exposed, developed in developer D-76 (developer prescribed by Eastman KodaK Co.) for 8 minutes at 20° C., fixed, washed and dried, and subjected to sensitometry, whereby the sensitivity and fog formed were determined. The results thus obtained are shown in Table 2 below.

TABLE 2

| | | Photographic Property | | | | Layer Strength | |
|---|---|---|---|---|---|---|---|
| | Addition Amount | After 7 days | | Acceleration Cond. (50° C., 2 days) | | Q | Scratch resistance |
| Compound | (per 100 g gelatin) | Relative sensitivity | Fog | Relative sensitivity | Fog | After 7 days | After 7 days |
| Control | 0 | 100 | 0.06 | 100 | 0.09 | 9.9 | 7 |
| Compound 1 of Invention | 25 m mol | 95 | 0.05 | 93 | 0.06 | 3.5 | 80 |
| Comparison | 5 m mol | 93 | 0.05 | 93 | 0.06 | 4.9 | 74 |

| | | Photographic Property | | | | Layer Strength | |
|---|---|---|---|---|---|---|---|
| | | After 7 days | | Acceleration Cond. (50° C., 2 days) | | Q | Scratch resistance |
| Compound | Addition Amount (per 100 g gelatin) | Relative sensitivity | Fog | Relative sensitivity | Fog | After 7 days | After 7 days |
| compound (V) | | | | | | | |

As is clear from the results shown in Table 2, the compound of this invention provides superior layer strength sufficient for practical use without reducing the photographic properties.

EXAMPLE 3

A silver iodobromide emulsion containing 3.0 mole% silver iodide was prepared and subjected to post ripening in the presence of sodium thiosulfate and a gold salt so that the highest sensitivity was obtained to provide a high speed negative working silver halide emulsion.

in a mixture of dibutyl phthalate and tricresyl phosphate was dissolved 1-(2',4',6'-trichlorophenyl)-3-[3''-(2''',4'''-di-t-amylphenoxyacetamido)benzamido]-5-pyrazolone and the solution was dispersed in o/w type in a gelatin solution using sorbitan monolaurate, Turkey red oil, and sodium dodecylbenzenesulfonate as a dispersing agent to provide a coupler emulsion. The coupler emulsion thus obtained was mixed with aforesaid silver halide emulsion. The thus obtained emulsion was divided into 3 equal parts and after adding to each of parts Compounds 1, 14 and 30, respectively, in an amount of 25 millimoles per 100 g of dry gelatin, each mixture was coated on a cellulose triacetate film base having a subbing layer at a dry thickness of about 10 μm and dried to provide color film samples each having a single layer of a magenta-forming coupler-containing photographic emulsion.

The color film sample was wedge exposed, color developed using 4-amino-3-methyl-N-ethyl-β-hydroxyethylaniline sesquisulfate.monohydrate as the color developing agent, and the coloring characteristics of the film were determined by a sensitometery.

The results show that the compound of this invention does not reduce the coloring property of the coupler and causes no color stain.

While the invention has been described in detail and with reference to specific embodiments thereof, it will be apparent to one skilled in the art that various changes and modifications can be made therein without departing from the spirit and scope thereof.

What is claimed is:

1. A hardening method for gelatin which comprises combining gelatin and, as a hardening agent a compound represented by formula (I):

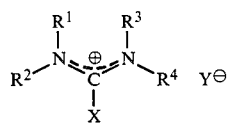

(I)

wherein $R^1$, $R^2$, $R^3$, and $R^4$, each represents a substituted or unsubstituted alkyl group, a substituted or unsubstituted alkenyl group, a substituted or unsubstituted aralkyl group, or a substituted or unsubstituted aryl group; or two of said $R^1$, $R^2$, $R^3$, and $R^4$ are combined with each other to form a ring (1); or 3 or more of said $R^1$, $R^2$, $R^3$ and $R^4$ are combined with each other to form a condensed ring (2); X represnts a group which is released when the compound shown by formula (I) reacts with a carboxylic acid group; $Y^\ominus$ represents an anion; or $Y^\ominus$ is combined with one of X, $R^1$, $R^2$, $R^3$, $R^4$, ring (1), or ring (2) to form an anionic portion of an intramolecular salt.

2. A hardening method as in claim 1, wherein the substituent of said substituted groups of $R^1$, $R^2$, $R^3$, or $R^4$ includes a substituent atom or group selected from the group consisting of a halogen atom, an alkoxy group, an aryloxy group, and N,N-di-substituted carbamoyl group, and said N,N-di-substituted carbamoyl group has substituents selected from the group consisting of an alkyl group, aralkyl group, and an aryl group.

3. A hardening method as in claim 1, wherein at least one combination of two members selected from the group consisting of $R^1$, $R^2$, $R^3$, and $R^4$ forms a nitrogen-containing heterocyclic ring.

4. A hardening method as in claim 1, wherein at least one combination of $R^1$ and $R^2$, and $R^3$ and $R^4$ forms a 5 to 8 membered nitrogen-containing heterocyclic ring.

5. A hardening method as in claim 4, wherein said nitrogen-containing heterocyclic ring is a ring selected from the group consisting of a pyrrolidine ring, a piperadine ring, a perphydroazepine ring, a morpholine ring, and a pyrrole ring.

6. A hardening method as in claim 1, wherein $R^1$ and $R^4$, and $R^3$ and $R^4$ are combined together to form pyrrolidine rings.

7. A hardening method as in claim 1, wherein a combination of $R^1$ and $R^3$ or $R^2$ and $R^4$ is combined together with the two nitrogen atoms N represented in formula (I) to form a 5 to 8 membered nitrogen-containing heterocyclic ring.

8. A hardening method as in claim 7, wherein said heterocyclic ring is selected from the group consisting of an imidazoline ring, a tetrahydropyrimidine ring, and a tetrahydrodiazepine ring.

9. A hardening method as in claim 1, wherein the compound having said condensed ring is reprensented by the formula;

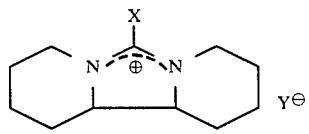

wherein X and $Y^\ominus$ are the same as defined in claim 1.

10. A hardening method as in claim 1, wherein X is an atom or group selected from the group consisting of a halogen atom, and a substituted or unsubstituted alkylsulfonyloxy group, a substituted or unsubstituted aralkylsulfonyloxy group, a substituted or unsubstituted arylsulfonyloxy group, and 1-pyperidinio group.

11. A hardening method as in claim 6, wherein X is chlorine atom.

12. A hardening method as in claim 1, wherein $Y^\ominus$ is an anion selected from the group consisting of a halide ion, a sulfonate ion, a sulfate ion, a phosphonate ion, a phosphate ion, $BF_4^\ominus$, $ClO_4^\ominus$, and $PF_6^\ominus$.

13. A hardening method as in claim 1, wherein said compound is used in an amount of from 0.01 to 20% by weight based on dry gelatin.

14. A hardening method as in claim 1, wherein said gelatin is contained in a light-sensitive photographic material.

15. A hardening method as in claim 14, wherein said light-sensitive photographic material is a silver halide photographic material.

16. A hardening method as in claim 15, wherein said compound is incorporated in at least one gelatin-containing layer selected from the group consisting of a silver halide emulsion layer, a subbing layer, a backing layer, a filter layer, an interlayer, and an overcoat layer of the silver halide photographic material.

* * * * *